US008317743B2

(12) United States Patent
Denenburg

(10) Patent No.: US 8,317,743 B2
(45) Date of Patent: Nov. 27, 2012

(54) MEDICAMENT MIXING AND INJECTION APPARATUS

(75) Inventor: Igor Denenburg, Gedera (IL)

(73) Assignee: Medimop Medical Projects Ltd., Ra'anana (IL)

( * ) Notice: Subject to any disclaimer, the term of this patent is extended or adjusted under 35 U.S.C. 154(b) by 263 days.

(21) Appl. No.: 12/678,928

(22) PCT Filed: Jul. 15, 2008

(86) PCT No.: PCT/US2008/070024

§ 371 (c)(1), (2), (4) Date: Mar. 18, 2010

(87) PCT Pub. No.: WO2009/038860

PCT Pub. Date: Mar. 26, 2009

(65) Prior Publication Data

US 2010/0204679 A1 Aug. 12, 2010

Related U.S. Application Data

(60) Provisional application No. 60/973,180, filed on Sep. 18, 2007.

(51) Int. Cl.
*A61M 37/00* (2006.01)

(52) U.S. Cl. ................ 604/82; 604/86; 604/87; 604/88; 604/89; 604/90; 604/91; 604/518

(58) Field of Classification Search ........................ None
See application file for complete search history.

(56) References Cited

U.S. PATENT DOCUMENTS

| | | | |
|---|---|---|---|
| 62,333 | A | 2/1867 | Holl |
| 1,704,817 | A | 3/1929 | Ayers |
| 1,930,944 | A | 10/1933 | Schmitz, Jr. |
| 2,326,490 | A | 8/1943 | Perelson |
| 2,931,668 | A | 4/1960 | Baley |

(Continued)

FOREIGN PATENT DOCUMENTS

| | | |
|---|---|---|
| DE | 1913926 A1 | 9/1970 |

(Continued)

OTHER PUBLICATIONS

Int'l Search Report issued Feb. 3, 2011 in Int'l Application No. PCT/IL2010/000777.

(Continued)

*Primary Examiner* — Jackie Ho
*Assistant Examiner* — Lauren M Peng
(74) *Attorney, Agent, or Firm* — Panitch Schwarze Belisario & Nadel LLP

(57) ABSTRACT

A method for mixing and injection and an apparatus for performing the method includes the use of a needle and a needle base, a syringe attachment element and a mixing chamber engagement assembly including a needle chamber surrounding the needle and a first liquid conduit portion, sealed from the needle chamber. A mixing chamber engagement portion includes a second liquid conduit portion communicating with the first liquid conduit portion and a mixing chamber. When the syringe attachment element and the needle base are in a first relative engagement orientation liquid can flow between an interior of the syringe and the first liquid conduit portion and upon axially displacing the needle base and syringe attachment element to a second relative engagement orientation, liquid can flow between an interior of the syringe and the needle.

7 Claims, 11 Drawing Sheets

U.S. PATENT DOCUMENTS 2,968,497 A 1/1961 Treleman
3,059,643 A 10/1962 Barton
D198,499 S 6/1964 Harautuneian
3,484,849 A 12/1969 Huebner et al.
3,618,637 A 11/1971 Santomieri
3,757,981 A 9/1973 Harris, Sr. et al.
3,826,261 A 7/1974 Killinger
3,885,607 A 5/1975 Peltier
3,957,052 A 5/1976 Topham
3,977,555 A 8/1976 Larson
3,993,063 A 11/1976 Larrabee
4,020,839 A 5/1977 Klapp
4,051,852 A 10/1977 Villari
4,109,670 A 8/1978 Slagel
4,187,848 A 2/1980 Taylor
4,210,173 A 7/1980 Choksi et al.
D257,286 S 10/1980 Folkman
4,253,501 A 3/1981 Ogle
4,296,786 A 10/1981 Brignola
4,314,586 A 2/1982 Folkman
4,328,802 A 5/1982 Curley et al.
D267,199 S 12/1982 Koenig
4,376,634 A 3/1983 Prior et al.
D271,421 S 11/1983 Fetterman
4,434,823 A 3/1984 Hudspith
4,475,915 A 10/1984 Sloane
4,493,348 A 1/1985 Lemmons
4,505,709 A 3/1985 Froning et al.
4,507,113 A 3/1985 Dunlap
D280,018 S 8/1985 Scott
4,532,969 A 8/1985 Kwaan
4,564,054 A 1/1986 Gustavsson
4,576,211 A 3/1986 Valentini et al.
4,588,396 A 5/1986 Stroebel et al.
4,588,403 A 5/1986 Weiss et al.
D284,603 S 7/1986 Loignon
4,604,093 A 8/1986 Brown et al.
4,607,671 A 8/1986 Aalto et al.
4,614,437 A 9/1986 Buehler
4,638,975 A 1/1987 Iuchi et al.
4,639,019 A 1/1987 Mittleman
4,667,927 A 5/1987 Oscarsson
4,676,530 A 6/1987 Nordgren et al.
4,697,622 A 10/1987 Swift et al.
4,721,133 A 1/1988 Sundblom
4,729,401 A 3/1988 Raines
4,743,229 A 5/1988 Chu
4,743,243 A 5/1988 Vaillancourt
4,758,235 A 7/1988 Tu
4,759,756 A 7/1988 Forman et al.
4,778,447 A 10/1988 Velde et al.
4,787,898 A 11/1988 Raines
4,834,152 A 5/1989 Howson et al.
4,865,592 A 9/1989 Rycroft
4,909,290 A 3/1990 Coccia
4,967,797 A 11/1990 Manska
D314,050 S 1/1991 Sone
4,997,430 A 3/1991 Van der Heiden et al.
5,035,686 A 7/1991 Crittenden et al.
5,041,105 A 8/1991 D'Alo et al.
5,045,066 A 9/1991 Scheuble et al.
5,049,129 A 9/1991 Zdeb et al.
5,053,015 A 10/1991 Gross
5,061,248 A 10/1991 Sacco
5,088,996 A 2/1992 Kopfer et al.
5,096,575 A 3/1992 Cosack
5,104,387 A 4/1992 Pokorney et al.
5,113,904 A 5/1992 Aslanian
5,122,124 A 6/1992 Novacek et al.
5,125,908 A 6/1992 Cohen
5,171,230 A 12/1992 Eland et al.
5,201,705 A 4/1993 Berglund et al.
5,201,717 A 4/1993 Wyatt et al.
5,203,771 A 4/1993 Melker et al.
5,203,775 A 4/1993 Frank et al.
5,211,638 A 5/1993 Dudar et al.
5,232,109 A 8/1993 Tirrell et al.
5,247,972 A 9/1993 Tetreault
5,269,768 A 12/1993 Cheung
5,270,219 A 12/1993 DeCastro et al.
5,279,576 A 1/1994 Loo et al.
5,288,290 A 2/1994 Brody
5,304,163 A 4/1994 Bonnici et al.
5,312,377 A 5/1994 Dalton
5,328,474 A 7/1994 Raines
5,334,163 A 8/1994 Sinnett
5,342,346 A 8/1994 Honda et al.
5,344,417 A 9/1994 Wadsworth, Jr.
5,350,372 A 9/1994 Ikeda et al.
5,364,387 A 11/1994 Sweeney
5,374,264 A 12/1994 Wadsworth, Jr.
5,385,547 A 1/1995 Wong et al.
5,397,303 A 3/1995 Sancoff et al.
5,445,630 A 8/1995 Richmond
5,445,631 A 8/1995 Uchida
5,464,123 A 11/1995 Scarrow
5,466,219 A 11/1995 Lynn et al.
5,466,220 A 11/1995 Brenneman
5,478,337 A 12/1995 Okamoto et al.
5,492,147 A 2/1996 Challender et al.
5,505,714 A 4/1996 Dassa et al.
5,509,433 A 4/1996 Paradis
5,520,659 A 5/1996 Hedges
5,526,853 A 6/1996 McPhee et al.
5,531,695 A 7/1996 Swisher
5,554,128 A 9/1996 Hedges
5,566,729 A 10/1996 Grabenkort et al.
5,569,191 A 10/1996 Meyer
5,573,281 A 11/1996 Keller
5,578,015 A 11/1996 Robb
5,583,052 A 12/1996 Portnoff et al.
5,584,819 A 12/1996 Kopfer
5,591,143 A 1/1997 Trombley, III et al.
5,607,439 A 3/1997 Yoon
5,611,576 A 3/1997 Guala
5,616,203 A 4/1997 Stevens
5,636,660 A 6/1997 Pfleiderer et al.
5,641,010 A 6/1997 Maier
5,647,845 A 7/1997 Haber et al.
5,651,776 A 7/1997 Appling et al.
5,653,686 A 8/1997 Coulter et al.
5,674,195 A 10/1997 Truthan
5,718,346 A 2/1998 Weiler
D393,722 S 4/1998 Fangrow, Jr. et al.
5,738,144 A 4/1998 Rogers
5,743,312 A 4/1998 Pfeifer et al.
5,746,733 A 5/1998 Capaccio et al.
5,755,696 A 5/1998 Caizza
5,772,630 A 6/1998 Ljungquist
5,772,652 A 6/1998 Zielinski
RE35,841 E 7/1998 Frank et al.
5,820,621 A 10/1998 Yale et al.
5,827,262 A * 10/1998 Neftel et al. .................. 604/414
5,832,971 A 11/1998 Yale et al.
5,833,213 A 11/1998 Ryan
5,834,744 A 11/1998 Risman
5,873,872 A 2/1999 Thibault et al.
5,879,337 A 3/1999 Kuracina et al.
5,879,345 A 3/1999 Aneas
5,887,633 A 3/1999 Yale et al.
5,893,397 A 4/1999 Peterson et al.
5,919,182 A 7/1999 Avallone
5,925,029 A 7/1999 Jansen et al.
5,944,700 A 8/1999 Nguyen et al.
5,971,965 A 10/1999 Mayer
5,989,237 A 11/1999 Fowles et al.
6,003,566 A 12/1999 Thibault et al.
6,004,278 A 12/1999 Botich et al.
6,063,068 A 5/2000 Fowles et al.
D427,308 S 6/2000 Zinger
6,080,132 A 6/2000 Cole et al.
6,090,093 A 7/2000 Thibault et al.
6,099,511 A 8/2000 Devos et al.
6,113,583 A 9/2000 Fowles et al.
6,139,534 A 10/2000 Niedospial, Jr. et al.
6,142,446 A 11/2000 Leinsing
6,156,025 A 12/2000 Niedospial, Jr. et al.

6,159,192 A 12/2000 Fowles et al.
6,171,293 B1 1/2001 Rowley et al.
6,174,304 B1 1/2001 Weston
6,221,041 B1 4/2001 Russo
6,221,054 B1 4/2001 Martin et al.
6,238,372 B1 5/2001 Zinger et al.
6,245,044 B1 6/2001 Daw et al.
D445,501 S 7/2001 Niedospial, Jr.
6,253,804 B1 7/2001 Safabash
6,258,078 B1 7/2001 Thilly
6,280,430 B1 8/2001 Neftel et al.
6,343,629 B1 2/2002 Wessman et al.
6,348,044 B1 2/2002 Coletti et al.
6,358,236 B1 3/2002 DeFoggi et al.
6,379,340 B1 4/2002 Zinger et al.
6,408,897 B1 6/2002 Laurent et al.
6,409,708 B1 6/2002 Wessman
6,453,956 B2 9/2002 Safabash
6,474,375 B2 11/2002 Spero et al.
6,478,788 B1 11/2002 Aneas
D468,015 S 12/2002 Horppu
6,503,240 B1 1/2003 Niedospial, Jr. et al.
6,503,244 B2 1/2003 Hayman
6,524,278 B1 2/2003 Campbell et al.
D472,316 S 3/2003 Douglas et al.
6,530,903 B2 3/2003 Wang et al.
D472,630 S 4/2003 Douglas et al.
6,544,246 B1 4/2003 Niedospial, Jr.
6,551,299 B2 4/2003 Miyoshi et al.
6,558,365 B2 5/2003 Zinger et al.
6,572,591 B2 6/2003 Mayer
6,575,955 B2 6/2003 Azzolini
6,581,593 B1 6/2003 Rubin et al.
6,582,415 B1 6/2003 Fowles et al.
6,591,876 B2 7/2003 Safabash
6,652,509 B1 11/2003 Helgren et al.
D483,487 S 12/2003 Harding et al.
D483,869 S 12/2003 Tran et al.
6,656,433 B2 12/2003 Sasso
6,666,852 B2 12/2003 Niedospial, Jr.
6,681,810 B2 1/2004 Weston
6,681,946 B1 1/2004 Jansen et al.
6,695,829 B2 2/2004 Hellstrom et al.
6,699,229 B2 3/2004 Zinger et al.
6,706,031 B2 3/2004 Manera
6,715,520 B2 4/2004 Andreasson et al.
6,729,370 B2 5/2004 Norton et al.
6,736,798 B2 5/2004 Ohkubo et al.
6,745,998 B2 6/2004 Doyle
6,746,438 B1 6/2004 Arnissolle
6,752,180 B2 6/2004 Delay
D495,416 S 8/2004 Dimeo et al.
D496,457 S 9/2004 Prais et al.
6,832,994 B2 12/2004 Niedospial, Jr. et al.
6,852,103 B2 2/2005 Fuller et al.
6,875,203 B1 4/2005 Fowles et al.
6,875,205 B2 4/2005 Leinsing
6,878,131 B2 4/2005 Novacek et al.
6,890,328 B2 5/2005 Fowles et al.
6,901,975 B2 6/2005 Aramata et al.
6,949,086 B2 9/2005 Ferguson et al.
RE38,996 E 2/2006 Crawford et al.
6,994,315 B2 2/2006 Ryan et al.
6,997,917 B2 2/2006 Niedospial, Jr. et al.
7,024,968 B2 4/2006 Raudabough et al.
7,074,216 B2 7/2006 Fowles et al.
7,083,600 B2 8/2006 Meloul
7,150,735 B2 12/2006 Hickle
7,192,423 B2 3/2007 Wong
7,294,122 B2 11/2007 Kubo et al.
D561,348 S 2/2008 Zinger et al.
7,326,194 B2 2/2008 Zinger et al.
7,350,764 B2 4/2008 Raybuck
7,354,422 B2 4/2008 Riesenberger et al.
7,354,427 B2 4/2008 Fangrow
7,425,209 B2 9/2008 Fowles et al.
7,435,246 B2 10/2008 Zihlmann
7,452,348 B2 11/2008 Hasegawa
7,470,265 B2 12/2008 Brugger et al.
7,488,297 B2 2/2009 Flaherty
7,491,197 B2 2/2009 Jansen et al.
7,523,967 B2 4/2009 Steppe
D595,420 S 6/2009 Suzuki et al.
D595,421 S 6/2009 Suzuki et al.
7,540,863 B2 6/2009 Haindl
7,540,865 B2 6/2009 Griffin et al.
D595,862 S 7/2009 Suzuki et al.
D595,863 S 7/2009 Suzuki et al.
7,611,487 B2 11/2009 Woehr et al.
7,611,502 B2 11/2009 Daly
7,628,779 B2 12/2009 Aneas
7,632,261 B2 12/2009 Zinger et al.
7,654,995 B2 2/2010 Warren et al.
7,695,445 B2 4/2010 Yuki
D616,090 S 5/2010 Kawamura
7,722,090 B2 5/2010 Burton et al.
D616,984 S 6/2010 Gilboa
7,731,678 B2 6/2010 Tennican et al.
7,743,799 B2 6/2010 Mosler et al.
7,758,082 B2 7/2010 Weigel et al.
7,771,383 B2 8/2010 Truitt et al.
7,799,009 B2 9/2010 Niedospial, Jr. et al.
7,803,140 B2 9/2010 Fangrow, Jr.
D630,732 S 1/2011 Lev et al.
7,862,537 B2 * 1/2011 Zinger et al. .................... 604/82
7,879,018 B2 2/2011 Zinger et al.
7,900,659 B2 3/2011 Whitley et al.
D637,713 S 5/2011 Nord et al.
8,066,688 B2 * 11/2011 Zinger et al. .................. 604/411
2001/0029360 A1 10/2001 Miyoshi et al.
2001/0051793 A1 12/2001 Weston
2002/0017328 A1 2/2002 Loo
2002/0066715 A1 6/2002 Niedospial
2002/0087118 A1 7/2002 Reynolds et al.
2002/0087141 A1 7/2002 Zinger et al.
2002/0087144 A1 7/2002 Zinger et al.
2002/0121496 A1 9/2002 Thiebault et al.
2002/0123736 A1 9/2002 Fowles et al.
2002/0127150 A1 9/2002 Sasso
2002/0173752 A1 11/2002 Polzin
2002/0193777 A1 12/2002 Aneas
2003/0036725 A1 2/2003 Lavi et al.
2003/0100866 A1 5/2003 Reynolds
2003/0120209 A1 6/2003 Jensen et al.
2003/0153895 A1 8/2003 Leinsing
2003/0195479 A1 10/2003 Kuracina et al.
2003/0199846 A1 10/2003 Fowles et al.
2003/0199847 A1 10/2003 Akerlund et al.
2004/0024354 A1 2/2004 Reynolds
2004/0044327 A1 3/2004 Hasegawa
2004/0073189 A1 4/2004 Wyatt et al.
2004/0153047 A1 8/2004 Blank et al.
2004/0181192 A1 9/2004 Cuppy
2004/0217315 A1 11/2004 Doyle
2004/0236305 A1 11/2004 Jansen et al.
2005/0124964 A1 6/2005 Niedospial et al.
2005/0137566 A1 6/2005 Fowles et al.
2005/0148994 A1 7/2005 Leinsing
2006/0030832 A1 2/2006 Niedospial et al.
2006/0079834 A1 4/2006 Tennican et al.
2006/0089594 A1 4/2006 Landau
2006/0089603 A1 4/2006 Truitt et al.
2006/0106360 A1 5/2006 Wong
2006/0135948 A1 6/2006 Varma
2006/0253084 A1 11/2006 Nordgren
2007/0060904 A1 3/2007 Vedrine et al.
2007/0079894 A1 4/2007 Kraus et al.
2007/0083164 A1 4/2007 Barrelle et al.
2007/0088252 A1 4/2007 Pestotnik et al.
2007/0088293 A1 4/2007 Fangrow
2007/0088313 A1 4/2007 Zinger et al.
2007/0106244 A1 5/2007 Mosler et al.
2007/0156112 A1 7/2007 Walsh
2007/0167904 A1 7/2007 Zinger et al.
2007/0191760 A1 8/2007 Iguchi et al.
2007/0191764 A1 8/2007 Zihlmann
2007/0191767 A1 8/2007 Hennessy et al.
2007/0219483 A1 9/2007 Kitani et al.

| | | | |
|---|---|---|---|
| 2007/0244461 A1 | 10/2007 | Fangrow | |
| 2007/0244462 A1 | 10/2007 | Fangrow | |
| 2007/0244463 A1 | 10/2007 | Warren et al. | |
| 2007/0255202 A1 | 11/2007 | Kitani et al. | |
| 2007/0265574 A1 | 11/2007 | Tennican et al. | |
| 2007/0265581 A1 | 11/2007 | Funamura et al. | |
| 2007/0270778 A9 | 11/2007 | Zinger et al. | |
| 2007/0287953 A1 | 12/2007 | Ziv et al. | |
| 2008/0009789 A1 * | 1/2008 | Zinger et al. | 604/89 |
| 2008/0172024 A1 | 7/2008 | Yow | |
| 2008/0249479 A1 | 10/2008 | Zinger et al. | |
| 2008/0249498 A1 | 10/2008 | Fangrow | |
| 2008/0312634 A1 | 12/2008 | Helmerson et al. | |
| 2009/0012492 A1 | 1/2009 | Zihlmann | |
| 2009/0054834 A1 * | 2/2009 | Zinger et al. | 604/84 |
| 2009/0082750 A1 | 3/2009 | Denenburg et al. | |
| 2009/0143758 A1 | 6/2009 | Okiyama | |
| 2009/0177177 A1 | 7/2009 | Zinger et al. | |
| 2009/0177178 A1 | 7/2009 | Pedersen | |
| 2009/0187140 A1 | 7/2009 | Racz | |
| 2009/0216212 A1 | 8/2009 | Fangrow, Jr. | |
| 2009/0299325 A1 | 12/2009 | Vedrine et al. | |
| 2009/0326506 A1 | 12/2009 | Hasegawa et al. | |
| 2010/0010443 A1 | 1/2010 | Morgan et al. | |
| 2010/0030181 A1 | 2/2010 | Helle et al. | |
| 2010/0036319 A1 | 2/2010 | Drake et al. | |
| 2010/0076397 A1 | 3/2010 | Reed et al. | |
| 2010/0087786 A1 * | 4/2010 | Zinger et al. | 604/224 |
| 2010/0137827 A1 | 6/2010 | Warren et al. | |
| 2010/0179506 A1 | 7/2010 | Shemesh et al. | |
| 2010/0204670 A1 | 8/2010 | Kraushaar et al. | |
| 2010/0228220 A1 * | 9/2010 | Zinger et al. | 604/414 |
| 2010/0241088 A1 | 9/2010 | Ranalletta et al. | |
| 2010/0286661 A1 | 11/2010 | Raday et al. | |
| 2010/0312220 A1 | 12/2010 | Kalitzki | |
| 2011/0230856 A1 | 9/2011 | Kyle et al. | |
| 2011/0264069 A1 | 10/2011 | Bochenko | |
| 2011/0276007 A1 * | 11/2011 | Denenburg | 604/198 |

FOREIGN PATENT DOCUMENTS

| | | | |
|---|---|---|---|
| DE | 4122476 | A1 | 1/1993 |
| DE | 19504413 | A1 | 8/1996 |
| DE | 202004012714 | U1 | 11/2004 |
| EP | 0192661 | A1 | 9/1986 |
| EP | 0195018 | A1 | 9/1986 |
| EP | 0258913 | A2 | 3/1988 |
| EP | 0416454 | A2 | 3/1991 |
| EP | 0518397 | A1 | 12/1992 |
| EP | 0521460 | A1 | 1/1993 |
| EP | 0637443 | A1 | 2/1995 |
| EP | 0737467 | A1 | 10/1996 |
| EP | 0806597 | A1 | 11/1997 |
| EP | 0814866 | A1 | 1/1998 |
| EP | 0898951 | A2 | 3/1999 |
| EP | 1008337 | A1 | 6/2000 |
| EP | 1029526 | A1 | 8/2000 |
| EP | 1051988 | A2 | 11/2000 |
| EP | 1329210 | A1 | 7/2003 |
| EP | 1454609 | A1 | 9/2004 |
| EP | 1454650 | A1 | 9/2004 |
| EP | 1498097 | A2 | 1/2005 |
| EP | 1872824 | A1 | 1/2008 |
| EP | 1930038 | A2 | 6/2008 |
| FR | 2029242 | A5 | 10/1970 |
| FR | 2869795 | A1 | 11/2005 |
| GB | 1444210 | A | 7/1976 |
| JP | 4329954 | A | 11/1992 |
| JP | 11503627 | T | 3/1999 |
| JP | 2003-102807 | A | 4/2003 |
| WO | 9403373 | A1 | 2/1994 |
| WO | 9507066 | A1 | 3/1995 |
| WO | 9600053 | A1 | 1/1996 |
| WO | 9629113 | A1 | 9/1996 |
| WO | 9832411 | A1 | 7/1998 |
| WO | 9837854 | A1 | 9/1998 |
| WO | 0128490 | A1 | 4/2001 |
| WO | 0130425 | A1 | 5/2001 |
| WO | 0132524 | A1 | 5/2001 |
| WO | 0160311 | A1 | 8/2001 |
| WO | 0191693 | A2 | 12/2001 |
| WO | 0209797 | A1 | 2/2002 |
| WO | 03051423 | A2 | 6/2003 |
| WO | 2004041148 | A1 | 5/2004 |
| WO | 2005105014 | A2 | 11/2005 |
| WO | WO 2005105014 | A2 * | 11/2005 |
| WO | 2007015233 | A1 | 2/2007 |
| WO | 2007105221 | A1 | 9/2007 |
| WO | 2009026443 | A2 | 2/2009 |
| WO | 2009029010 | A1 | 3/2009 |
| WO | 2009038860 | A2 | 3/2009 |
| WO | 2009040804 | A2 | 4/2009 |
| WO | 2009087572 | A1 | 7/2009 |
| WO | 2009093249 | A1 | 7/2009 |
| WO | 2009112489 | A1 | 9/2009 |

OTHER PUBLICATIONS

Int'l Search Report issued on Mar. 17, 2011 in Int'l Application No. PCT/IL2010/000854.

http://www.knovel.com/web/portal/browse/display?_EXT_KNOVEL_DISPLAY_bookid=1023&VerticalID=0 [retrieved on Feb. 9, 2011].

Int'l Search Report issued on Mar. 17, 2011 in Int'l Application No. PCT/IL2010/00915.

Office Action Issued May 12, 2011 in U.S. Appl. No. 12/063,176.

Office Action issued Jul. 11, 2011 in U.S. Appl. No. 12/293,122.

Int'l Search Report issued Jul. 12, 2011 in Int'l Application No. PCT/IL2011/000187.

Int'l Search Report issued Jul. 12, 2011 in Int'l Application No. PCT/IL2011/000186.

Office Action issued Aug. 3, 2011 in JP Application No. 2008-525719.

Int'l Search Report issued Oct. 7, 2011 in Int'l Application No. PCT/IL2011/000511.

Office Action issued Nov. 12, 2010 in U.S. Appl. No. 29/334,697.

The MixJect transfer system, as shown in the article, "Advanced Delivery Devices," Drug Delivery Technology Jul./Aug. 2007 vol. 7 No. 7 [on-line]. [Retrieved from Internet May 14, 2010.] URL: <http://www.drugdeiverytech-online.com/drugdelivery/200707/?pg=28pg28>. (3 pages).

Publication date of Israeli Patent Application 186290 [on-line]. ]Retrieved from Internet May 24, 2010]. URL:<http://www.ilpatsearch.justrice.gov.il/UI/RequestsList.aspx>. (1 page).

Int'l Search Report issued Nov. 25, 2010 in Int'l Application No. PCT/IL2010/000530.

Office Action issued Feb. 7, 2011 in U.S. Appl. No. 12/783,194.

Office Action issued Dec. 20, 2010 in U.S. Appl. No. 12/063,176.

Office Action issued Dec. 13, 2010 in U.S. Appl. No. 12/293,122.

Office Action issued Nov. 29, 2010 in U.S. Appl. No. 11/568,421.

Office Action issued Dec. 23, 2010 in U.S. Appl. No. 29/334,696.

Int'l Search Report issued Mar. 6, 2012 in Int'l Application No. PCT/IL2011/000834; Written Opinion.

Office Action issued Mar. 1, 2012 in JP Application No. 2007-510229.

Int'l Search Report issued Mar. 7, 2012 in Int'l Application No. PCT/IL2011/000829; Written Opinion.

Office Action issued Mar. 13, 2012 in CA Application No. 2,563,643.

Office Action issued Mar. 1, 2012 in CN Application No. 2008801108283.4.

U.S. Appl. No. 13/498,378 by LEV, filed Mar. 27, 2012.

Int'l Search Report issued Mar. 17, 2011 in Int'l Application No. PCT/IL2010/000854; Written Opinion.

Int'l Search Report issued Mar. 17, 2011 in Int'l Application No. PCT/IL2010/000915; Written Opinion.

U.S. Appl. No. 13/505,790 by LEV, filed May 3, 2012.

U.S. Appl. No. 13/505,881 by LEV, filed May 3, 2012.

http://www.westpharma.com/eu/en/products/Pages/Mixject.aspx (admitted prior art), Jul. 10, 2012.

http://www.westpharma.com/eu/SiteCollectionDocuments/Recon/mixject%20product%20sheet.pfg: MIXJECT product information sheet pp. 1 (admitted prior art), Jul. 10, 2012.

Written Opinion of the ISR Issued Oct. 17, 2009 in Int'l Application No. PCT/IL08/00517.

Office Action Issued Jan. 20, 2010 in JP Application No. 2007-510229.
U.S. Appl. No. 13/522,410 by LEV, filed Jul. 16, 2012.
U.S. Appl. No. 13/576,461 by LEV, filed Aug. 1, 2012.
Office Action issued Jun. 14, 2012 in U.S. Appl. No. 29/376,980.
Office Action issued Jun. 15, 2012 in U.S. Appl. No. 29/413,170.
Office Action issued Jun. 21, 2012 in U.S. Appl. No. 12/596,167.
Grifols Vial Adapter Product Literature, 2 pages, Jan. 2002. cited by other.
Novel Transfer, Mixing and Drug Delivery Systems, MOP Medimop Medical Projects Ltd. Catalog, 4 pages, Rev. 4, 2004. cited by other.
Smart Site.RTM. Alaris Medical Systems Product Brochure, 4 pages, Issue 1, Oct. 1999. cited by other.
Smart Site.RTM. Needle Systems, Alaris Medical Systems Webpage, 4 pages, Feb. 2006. cited by other.
Photographs of Alaris Medical Systems SmartSite.RTM. device, 5 pages, 2002. cited by other.
Non-Vented Vial Access Pin with ULTRASITE.RTM. Valve, B. Braun Medical, Inc. website and product description, 3 pages, Feb. 2006. cited by other.
Office Action Issued Oct. 6, 2003 in U.S. Appl. No. 10/062,796.
Office Action Issued Feb. 22, 2005 in U.S. Appl. No. 10/062,796.
Office Action Issued Oct. 5, 2005 in U.S. Appl. No. 10/062,796.
Office Action Issued Feb. 20, 2009 in U.S. Appl. No. 11/694,297.
Int'l Search Report Issued Dec. 6, 2006 in Int'l Application No. PCT/IL2006/000912.
Int'l Preliminary Report on Patentability Issued Dec. 4, 2007 in Int'l Application No. PCT/IL2006/000912.
http://www.westpharma.com/eu/en/products/Pages/Mixject.aspx, Sep. 10, 2010.
http://www.westpharma.com/eu/SiteCollectionDocuments/Recon/mixject%20product%20sheet.pfg: MIXJECT product information sheet pp. 1, Sep. 10, 2010.
Int'l Search Report Issued Jul. 27, 2007 in Int'l Application No. PCT/IL2007/000343.
Int'l Preliminary Report on Patentability Issued Jun. 19, 2008 in Int'l Application No. PCT/IL2007/000343.
Int'l Search Report Issued Mar. 27, 2009 in Int'l Application No. PCT/US2008/070024.
Int'l Search Report Issued Oct. 17, 2005 in Int'l Application No. PCT/IL2005/000376.
Int'l Preliminary Report on Patentability Issued Jun. 19, 2006 in Int'l Application No. PCT/IL2005/000376.
Written Opinion of ISR Issued in Int'l Application No. PCT/IL2005/000376, Oct. 29, 2006.
Int'l Search Report Issued Aug. 25, 2008 in Int'l Application No. PCT/IL2008/000517.
Written Opinion of the ISR Issued in Int'l Application No. PCT/IL08/00517, Oct. 17, 2009.
Int'l Preliminary Report on Patenability Issued Oct. 20, 2009 in Int'l Application No. PCT/IL2008/000517.
Written Opinion of the Int'l Searching Authority Issued Oct. 27, 2008 in Int'l Application No. PCT/US2008/070024.
Int'l Search Report Issued Mar. 12, 2009 in Int'l Application No. PCT/IL2008/001278.
Office Action Issued in JP Application No. 2007-510229, Jan. 20, 2010.
Office Action Issued Apr. 20, 2010 in U.S. Appl. No. 11/997,569.
Int'l Search Report dated Nov. 20, 2006 in Int'l Application No. PCT/IL2006/000881.
Office Action Issued May 27, 2010 in U.S. Appl. No. 11/559,152.
Decision to Grant mailed Apr. 12, 2010 in EP Application No. 08738307.1.
Office Action issued Jun. 1, 2010 in U.S. Appl. No. 11/568,421.

* cited by examiner

MEDICAMENT MIXING AND INJECTION APPARATUS

CROSS-REFERENCE TO RELATED APPLICATION

This application is a Section 371 of International Application No. PCT/US2008/070024, filed Jul. 15, 2008, which was published in the English language on Mar. 26, 2009 under International Publication No. WO 2009/038860 A3, and the disclosure of which is incorporated herein by reference.

FIELD OF THE INVENTION

The invention pertains to liquid drug injection devices generally.

BACKGROUND OF THE INVENTION

The following patent documents are believed to represent the current state of the art:

U.S. Pat. Nos. 5,584,819; 5,746,733; 5,755,696; 5,820,621; 5,827,262; 5,832,971; 5,887,633; 5,919,182; 6,238,372; 6,280,430; 6,524,278; 6,729,370; US2007/0088313; US2007/0167904; US2007/0270778 and US2008/0009789.

SUMMARY OF THE INVENTION

The present invention seeks to provide an improved medicament mixing and injection apparatus.

There is thus provided in accordance with a preferred embodiment of the present invention medicament mixing and injection apparatus comprising an injection needle assembly including a needle extending along an injection axis and a needle base to which said needle is fixed, a syringe attachment element configured at a first axial end thereof to receive a needleless syringe and a second axial end thereof to engage the needle base in at least first and second relative engagement orientations which are mutually axially separated along the injection axis and a medicament mixing chamber engagement assembly including an intermediate portion having a hand-engageable portion, the intermediate element including a needle chamber surrounding the needle and a first liquid conduit portion, sealed from the needle chamber and a medicament mixing chamber engagement portion including a second liquid conduit portion communicating with the first liquid conduit portion and configured for communication with a medicament mixing chamber, the syringe attachment element and the needle base being configured to permit liquid communication between an interior of the needleless syringe and the first liquid conduit portion when the syringe attachment element and the needle base are in the first relative engagement orientation and to permit liquid communication between an interior of the needleless syringe and the needle when the syringe attachment element and the needle base are in the second relative engagement orientation, axially separated from the first relative orientation along said injection axis.

In accordance with a preferred embodiment of the present invention medicament mixing and injection apparatus operation of the hand engageable portion enables relative axial movement of the needle base and the syringe attachment portion from the first relative orientation along said injection axis to the second relative orientation along the injection axis.

In accordance with a preferred embodiment of the present invention the intermediate portion and the medicament mixing chamber engagement portion are formed as separate elements or as one piece.

Preferably, a medicament mixing and injection method comprising providing a medicament mixing and injection assembly including a needle extending along an injection axis and a needle base to which said needle is fixed, a syringe attachment element configured at a first axial end thereof to receive a needleless syringe and an a second axial end thereof to engage the needle base in at least first and second relative engagement orientations which are mutually axially separated along the injection axis and a medicament mixing chamber engagement assembly associating a medicament mixing chamber with the medicament mixing chamber engagement assembly, attaching a syringe to the syringe attachment element, mixing a medicament in the medicament mixing chamber when the syringe attachment element and the needle base are in the first relative engagement orientation and drawing mixed medicament into the syringe, providing relative axial displacement of the needle base and the syringe attachment element along the injection axis such that the syringe attachment element and the needle base are in the second relative engagement orientation, disengaging the medicament mixing chamber engagement assembly from the syringe attachment element and injecting the mixed medicament from the syringe through the needle.

In accordance with a preferred embodiment of the present invention the medicament mixing chamber engagement assembly includes a needle chamber surrounding the needle and a liquid conduit portion, sealed from the needle chamber and the syringe attachment element and the needle base are configured to permit liquid communication between an interior of the needleless syringe and the first liquid conduit portion when the syringe attachment element and the needle base are in the first relative engagement orientation and to permit liquid communication between an interior of the needleless syringe and the needle when the syringe attachment element and the needle base are in the second relative engagement orientation, axially separated from the first relative orientation along the injection axis.

In accordance with a preferred embodiment of the present invention the medicament mixing chamber engagement assembly includes a hand engageable portion which selectably enables relative axial movement of the needle base and the syringe attachment portion from the first relative orientation along the injection axis to the second relative orientation along the injection axis.

BRIEF DESCRIPTION OF THE DRAWINGS

The present invention will be understood and appreciated more fully from the following detailed description.

DETAILED DESCRIPTION OF THE INVENTION

Reference is now made to FIGS. 1-11H which illustrate the structure and operation of medicament mixing and injection apparatus constructed and operative in accordance with a preferred embodiment of the present invention.

Figure 1:
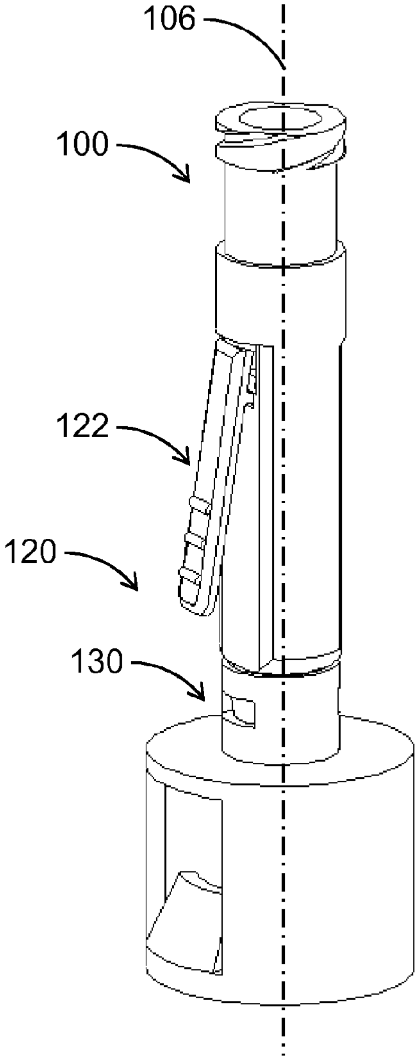
FIGS. 1 and 2 are simplified perspective assembled and exploded view illustrations of medicament mixing and injection apparatus constructed and operative in accordance with a preferred embodiment of the present invention.
Figure 2:
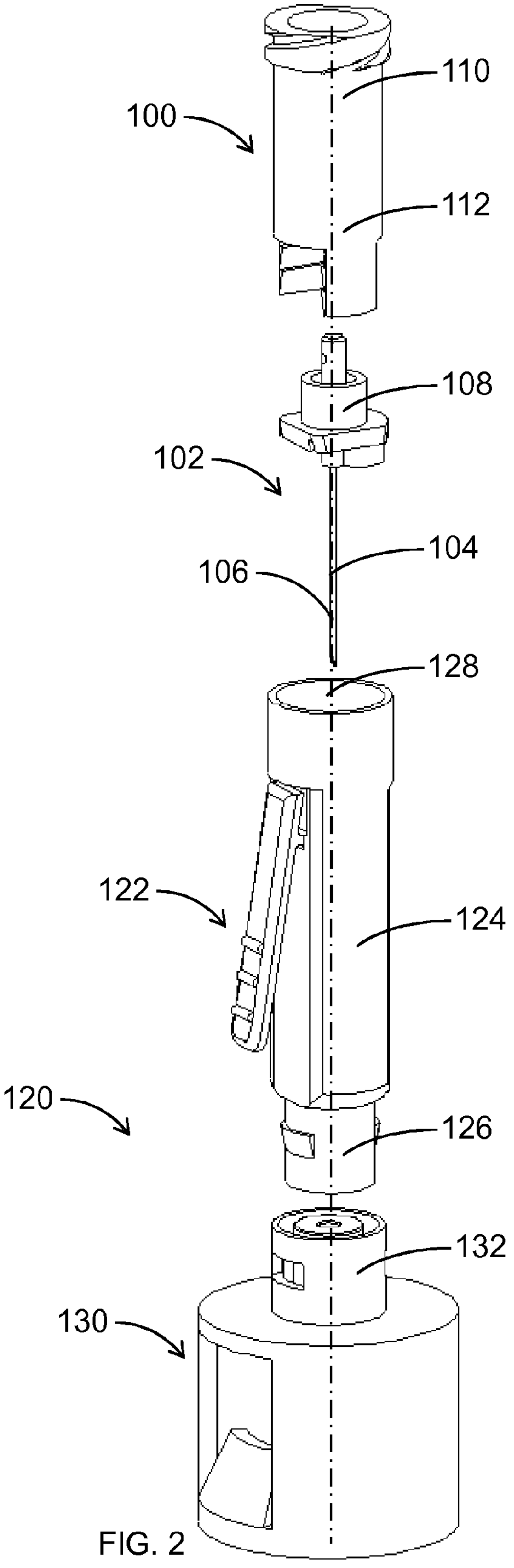
Figure 3A:
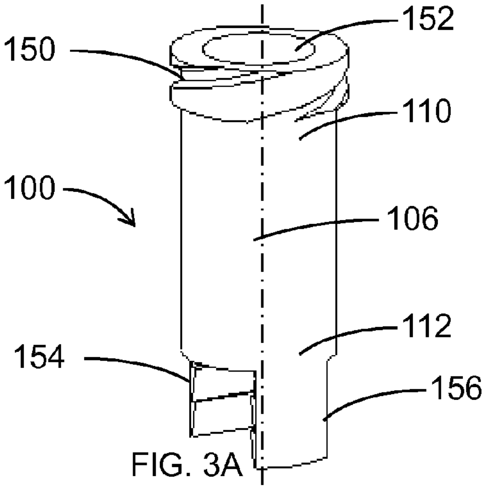
FIGS. 3A, 3B and 3C are simplified pictorial illustrations of a syringe attachment element useful in the apparatus of FIGS. 1 & 2.
Figure 3B:
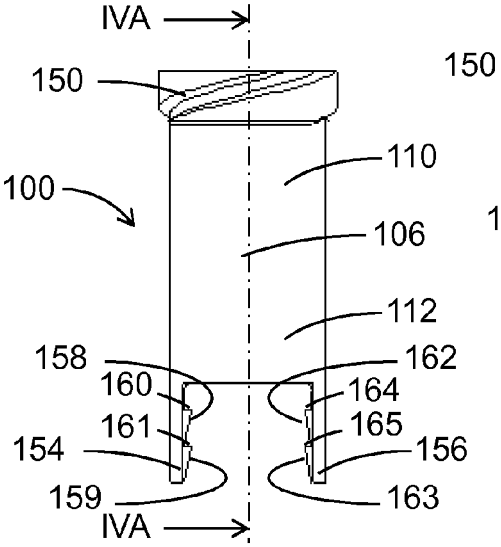
Figure 3C:
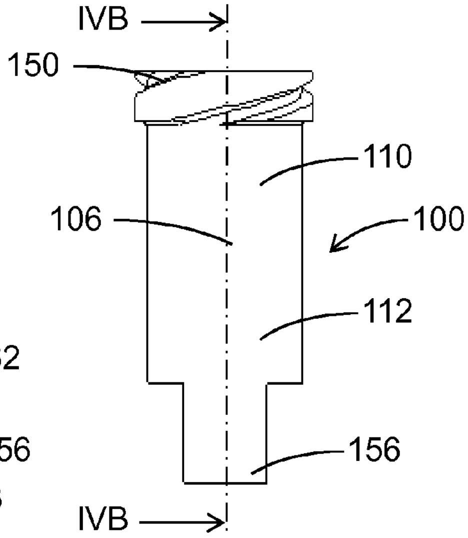
Figure 4A:
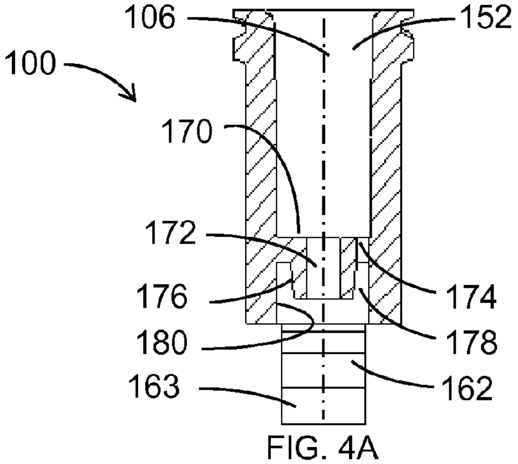
FIGS. 4A and 4B are sectional illustrations taken along lines IVA-IVA and IVB-IVB in FIGS. 3B and 3C.
Figure 4B:
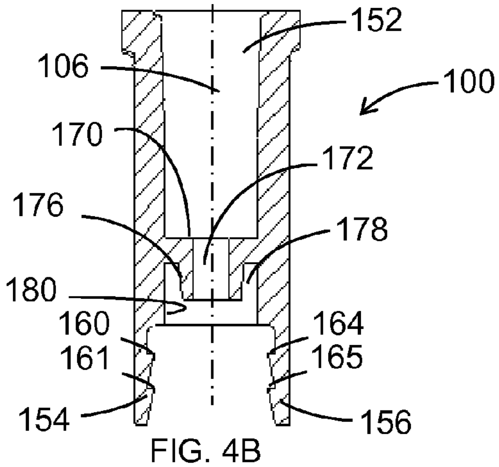

FIGS. 1 and 2 are simplified perspective assembled and exploded view illustrations of medicament mixing and injection apparatus constructed and operative in accordance with a preferred embodiment of the present invention. As see in FIGS. 1 and 2, the medicament mixing and injection apparatus preferably includes a syringe attachment element 100 and an injection needle assembly 102 including a needle 104 extending along an injection axis 106 and a needle base 108 to which the needle is fixed, typically by an adhesive.

In accordance with a preferred embodiment of the present invention, the syringe attachment element 100 is configured at a first axial end 110 thereof to receive a needleless syringe (not shown) and an a second axial end 112 thereof to engage the needle base 108 in at least first and second relative engagement orientations which are mutually axially separated along the injection axis 106.

The medicament mixing and injection apparatus also preferably includes a medicament mixing chamber engagement assembly 120 including a first portion 122 having a hand-engageable portion 124, the intermediate element preferably including a needle chamber 128 surrounding the needle 104 and a first liquid conduit portion 126, sealed from the needle chamber 128 and medicament mixing chamber engagement portion 130 including a second liquid conduit portion 132 communicating with the first liquid conduit portion 126 and configured for communication with a medicament mixing chamber (not shown), which may be, for example a vial or ampoule and may alternatively be any other suitable medicament mixing chamber.

In the illustrated embodiment, portions 122 and 130 are shown as separate elements, it being appreciated that alternatively they may be formed as a unitary element.

In accordance with a preferred embodiment of the present invention, the syringe attachment element 100 and the needle base 108 are configured to permit liquid communication between an interior of the needleless syringe (not shown) and the first liquid conduit portion 122 when the syringe attachment element 100 and the needle base 108 are in the first relative engagement orientation and to permit liquid communication between an interior of the needleless syringe (not shown) and the needle 104 when the syringe attachment element 100 and the needle base 108 are in the second relative engagement orientation, axially separated from the first relative orientation along the injection axis.

Preferably when the syringe attachment element 100 and the needle base 108 are in the first relative engagement orientation, liquid from the interior of the needleless syringe (not shown) is prevented from reaching the needle 104 and when the syringe attachment element 100 and the needle base 108 are in the second relative engagement orientation, axially separated from the first relative orientation along the injection axis, liquid from the interior of the needleless syringe (not shown) is prevented from reaching the first liquid conduit portion 122.

FIGS. 3, 3A, 3B, 4A and 4B, illustrate a preferred embodiment of syringe attachment element 100. As seen particularly in FIGS. 3-4B, the syringe attachment element 100 is a generally cylindrical element defining a Luer lock at end 110 and having an external threading 150 at end 110 thereof and a generally conical internal passageway 152 opening at end 110.

First and second generally axially extending engagement tabs 154 and 156 are provided at end 112 of the syringe attachment element 100. Tab 154 has inwardly facing end portions 158, 159, each having a generally truncated conical cross-section and defining a retaining shoulder surface 160, 161. Tab 156 has inwardly facing portions 162, 163, each having a generally truncated conical cross-section and defining a retaining shoulder surface 164, 165.

Passageway 152 terminates in a bulkhead 170 which defines a generally central bore 172 and a side bore 174. Generally central bore 172 is partially defined by an axial portion having a generally truncated conical exterior wall surface 176. Surrounding wall surface 176 and extending to end 112 is a recess 178 bounded by a cylindrical wall 180 surface.

Figure 5A:
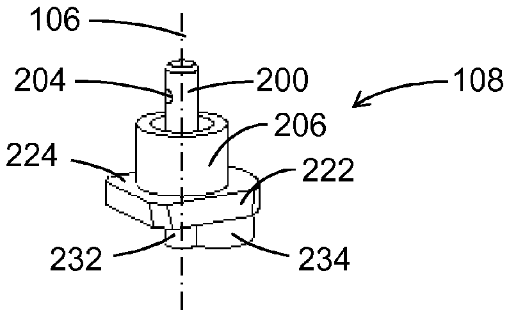
FIGS. 5A, 5B and 5C are simplified pictorial illustrations of a needle base useful in the apparatus of FIGS. 1 & 2.
Figure 5B:
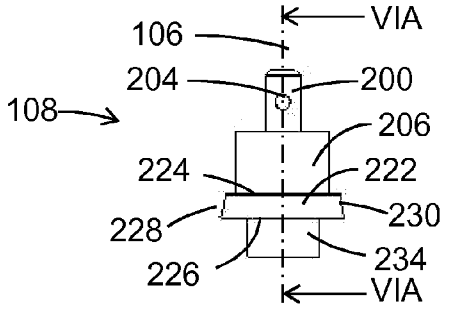
Figure 5C:
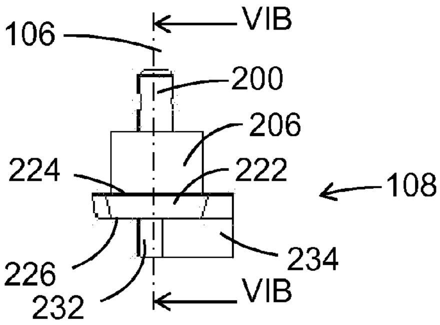
Figure 6A:
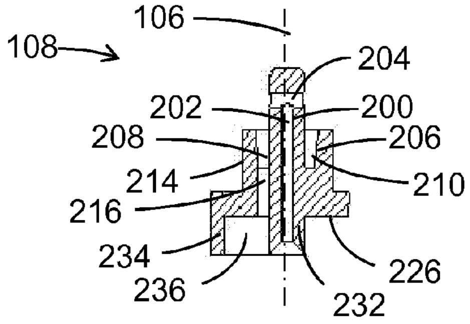
FIGS. 6A and 6B are sectional illustrations taken along lines VIA-VIA and VIB-VIB in FIGS. 5B and 5C.
Figure 6B:
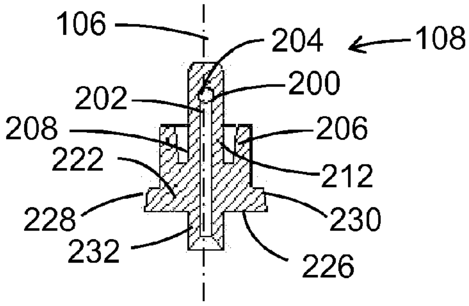
Figure 7A:
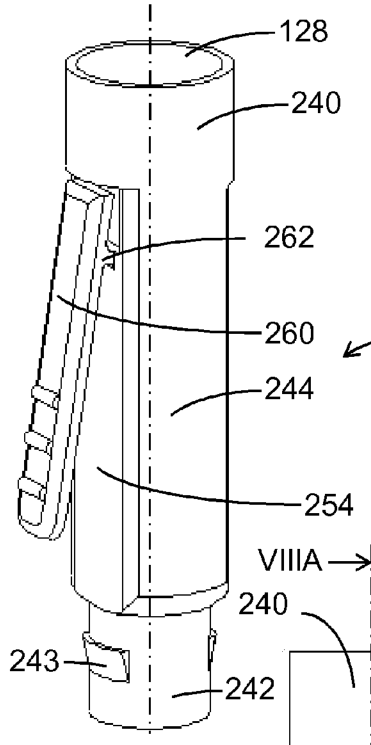
FIGS. 7A, 7B, 7C, 7D, 7E and 7F are simplified pictorial illustrations of a first portion of a medicament mixing chamber engagement assembly useful in the apparatus of FIGS. 1 & 2.
Figure 7B:
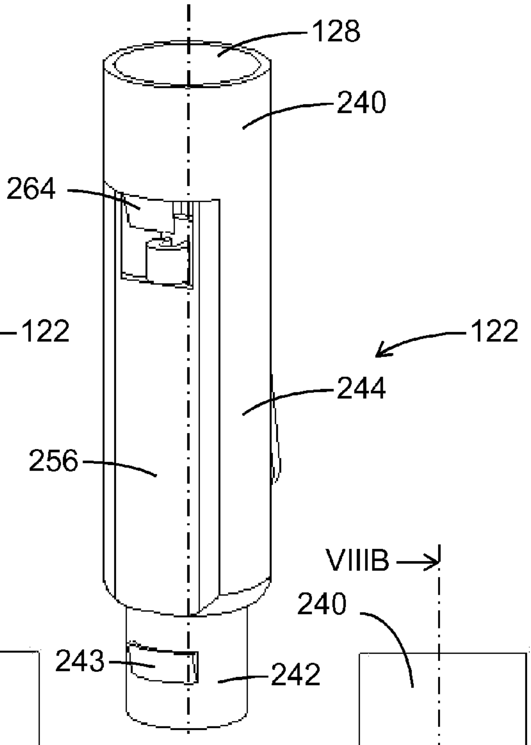
Figure 7C:
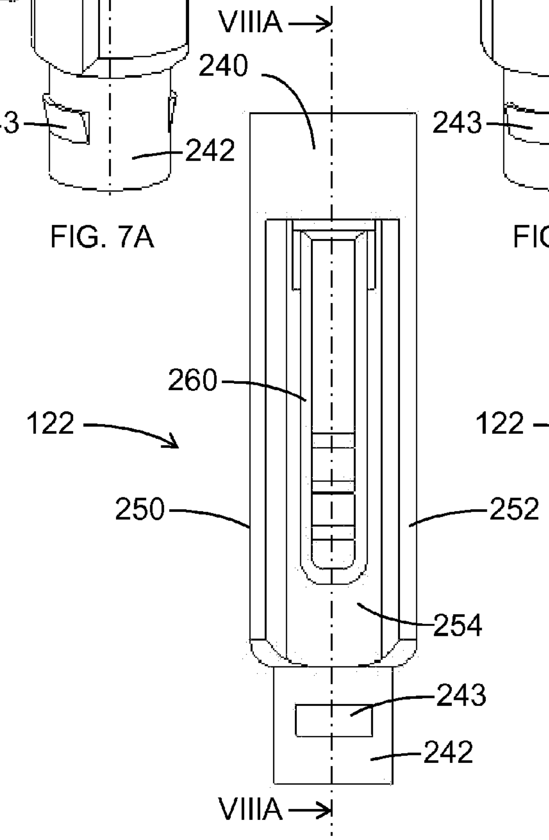
Figure 7D:
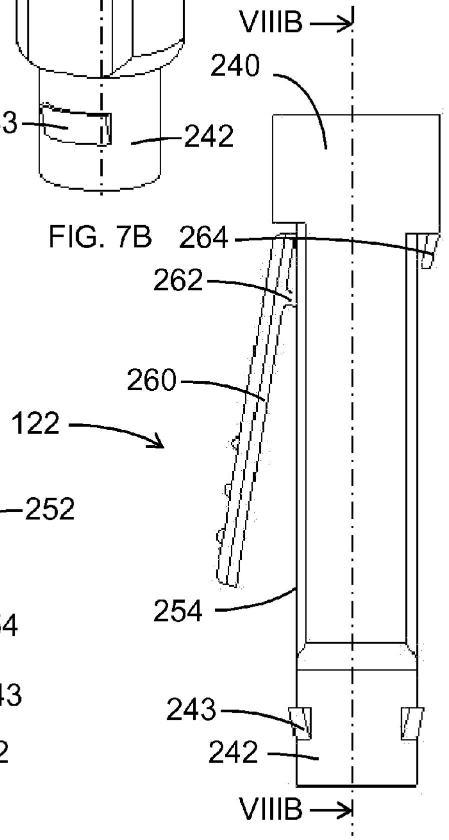
Figure 7E:
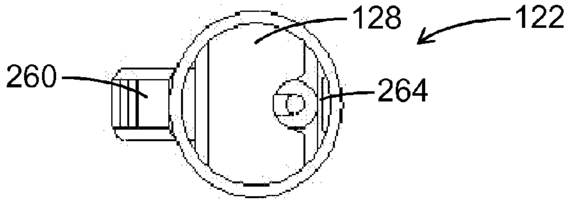
Figure 7F:
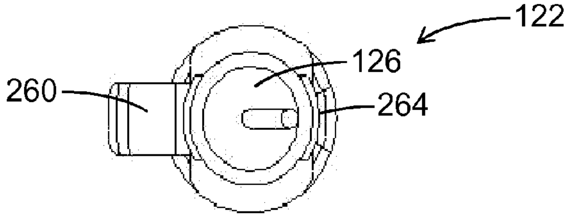
Figure 8A:
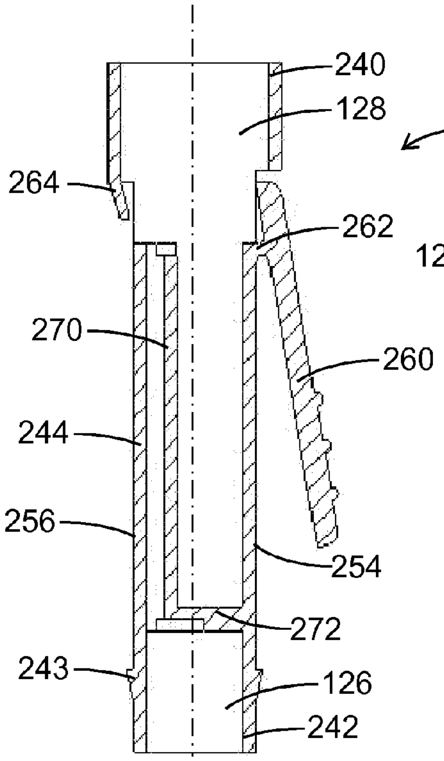
FIGS. 8A and 8B are sectional illustrations taken along lines VIIIA-VIIIA and VIIIB-VIIIB in FIGS. 7C and 7D.
Figure 8B:
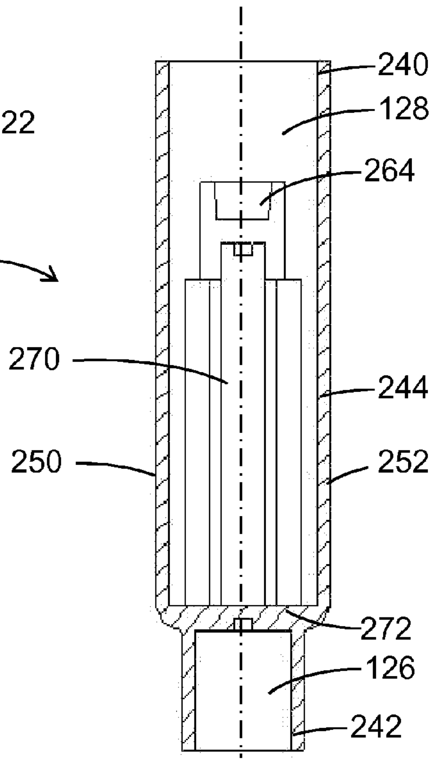

FIGS. 5, 5A, 5B, 6A and 6B illustrate a preferred embodiment of needle base 108. As seen in FIGS. 5-6B, the needle base 108 is preferably a unitary element, typically injection molded and includes a central cylindrical portion 200 formed with an axial needle retaining bore 202, arranged to receive and retain needle 104 (not shown) along injection axis 106, which communicates with a liquid communications bore 204.

Surrounding part of central cylindrical portion 200 is an intermediate cylindrical portion 206 in which is formed an annular recess 208 bounded by a generally conical wall surface 210 of a wall 212 whose outer surface forms part of an outer cylindrical wall surface 214 of intermediate cylindrical portion 206. Cylindrical portion 200 is sized and configured so as to be axially slidable into engagement with recess 178, when the syringe attachment element 100 and the needle base 108 are in the second relative engagement orientation. In this orientation, that part of central cylindrical portion 200 which extends axially beyond intermediate cylindrical portion 206 slidingly and sealingly engages generally bore 172 of the syringe attachment element.

A liquid conduit 216 extends from recess 208 generally parallel to the injection axis 106 through parts of the intermediate cylindrical portion 206 and through a base portion 222, through which axial needle retaining bore 202 also extends.

Base portion 222 defines a generally planar shoulder surface 224 and an opposite generally planar surface 226 and conical edge surfaces 228 and 230.

Extending parallel to injection axis 106 from generally planar surface 226 are typically formed first and second merged cylinders 232 and 234. Cylinder 232 is preferably centered about the injection axis 106 and axial needle retaining bore 202 extends therethrough. Cylinder 234 defines a generally cylindrical recess 236 which communicates with the liquid conduit 216.

FIGS. 7A, 7B, 7C, 7D, 7E, 7F, 8A and 8B illustrate a preferred embodiment of first portion 122, which is preferably a generally cylindrical element preferably including a first, generally circular cylindrical portion 240 arranged for removable engagement with the syringe attachment element 100, and a second generally circular cylindrical portion 242, formed with an externally facing conical flange 243 and arranged for retaining the medicament mixing chamber engagement portion 130. Intermediate portions 240 and 242 is a hand engageable portion 244 having generally oppositely facing curved side wall portions 250 and 252 separated by generally flat wall portions 254 and 256.

Hand engageable portion 244 preferably includes a hand engageable lever 260 which is pivotably joined to generally flat wall portion 254 and defines a selectably positionable retaining edge 262. Disposed generally opposite to hand engageable lever 260 and extending over a portion of generally flat wall portion 256 is an inwardly facing retaining protrusion 264.

Interiorly of hand engageable portion 244, there is preferably provided a wall 270, extending generally parallel to the injection axis 106, which terminates in a wall 272 extending perpendicularly to the injection axis 106. Walls 270 and 272 preferably separate first liquid conduit portion 126 and needle chamber 128, which is separated therefrom by walls 270 and 272.

Figure 9A:
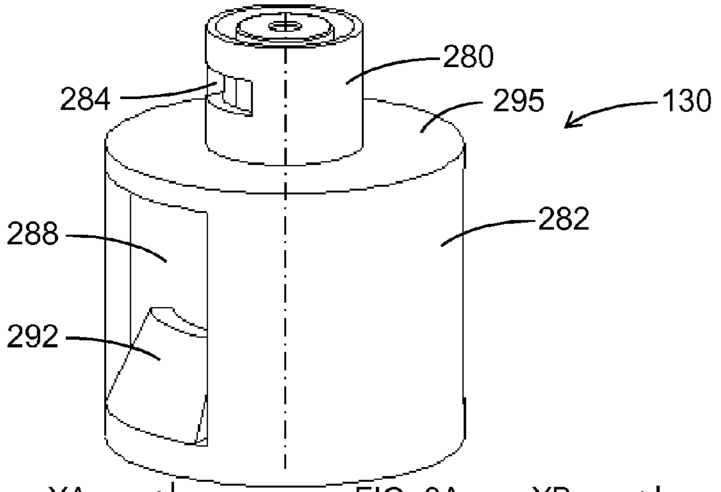
FIGS. 9A, 9B and 9C are simplified pictorial illustration of a second portion of a medicament mixing chamber engagement assembly useful in the apparatus of FIGS. 1 & 2.
Figure 9B:
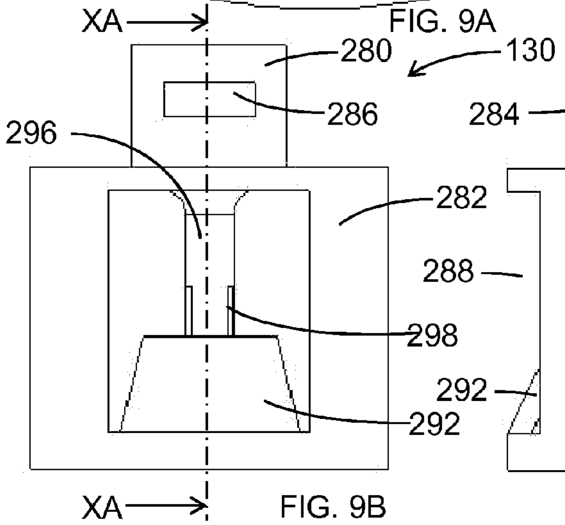
Figure 9C:
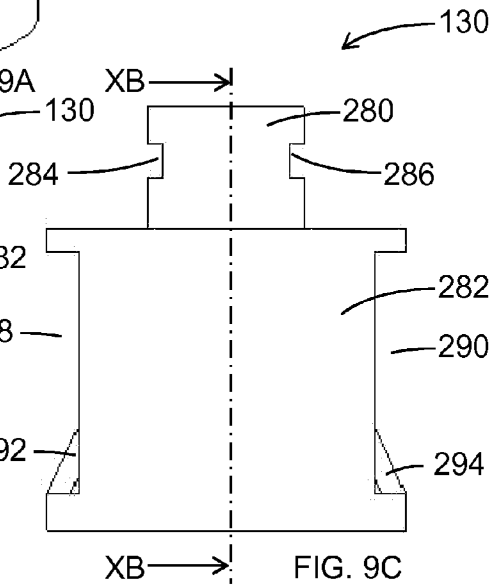
Figure 10A:
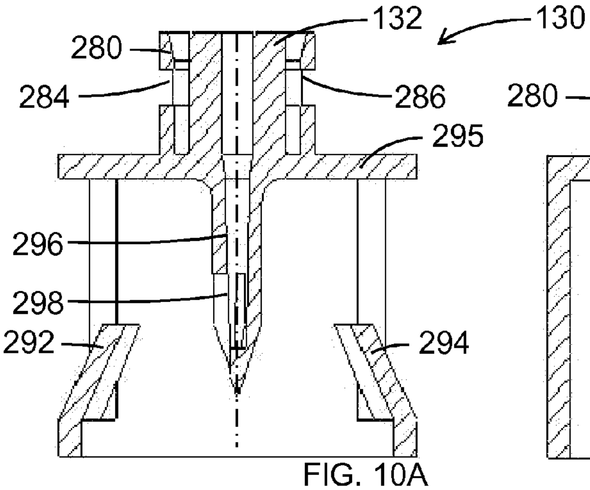
FIGS. 10A and 10B are sectional illustrations taken lines XA-XA and XB-XB in FIGS. 9B and 9C.
Figure 10B:
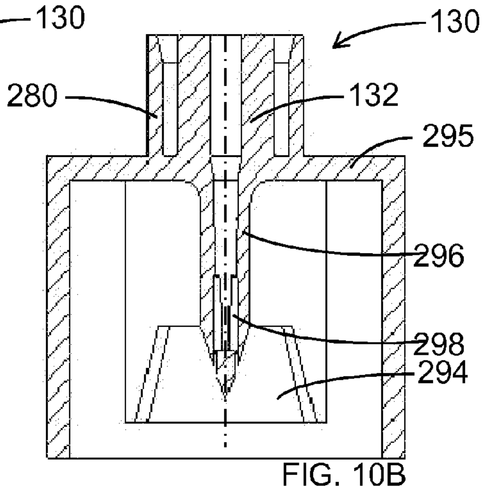

FIGS. 9, 9A, 9B, 10A and 10B illustrate a preferred embodiment of the second portion 130. As seen in FIGS. 9-10B, a second portion 130 including a second liquid conduit portion 132 communicating with the first liquid conduit portion 126 and configured for communication with a medicament mixing chamber (not shown), which may be, for example a vial or ampoule and may alternatively be any other suitable medicament mixing chamber.

It is seen that second portion 130 is including a first, generally circular cylindrical portion 280 preferably formed with a pair of oppositely placed windows 284 and 286 for retaining the first portion 122, and a second generally circular cylindrical portion 282 preferably formed with a pair of oppositely placed windows 288 and 290, and an inwardly facing retaining protrusions 292 and 294, for communication with a medicament mixing chamber (not shown), separated by bulkhead 295 having defined at its center a hollow spike 296. In use, spike 296 punctures the elastomeric seal of a medicament mixing chamber (not shown), thereby to enable fluid communication between the medicament mixing chamber (not shown) and the interior of syringe (not shown) via apertures 298 formed at a forward end of spike 296.

Figures 11A, 11B, 11C, 11D, 11E, 11F, 11G, 11H:
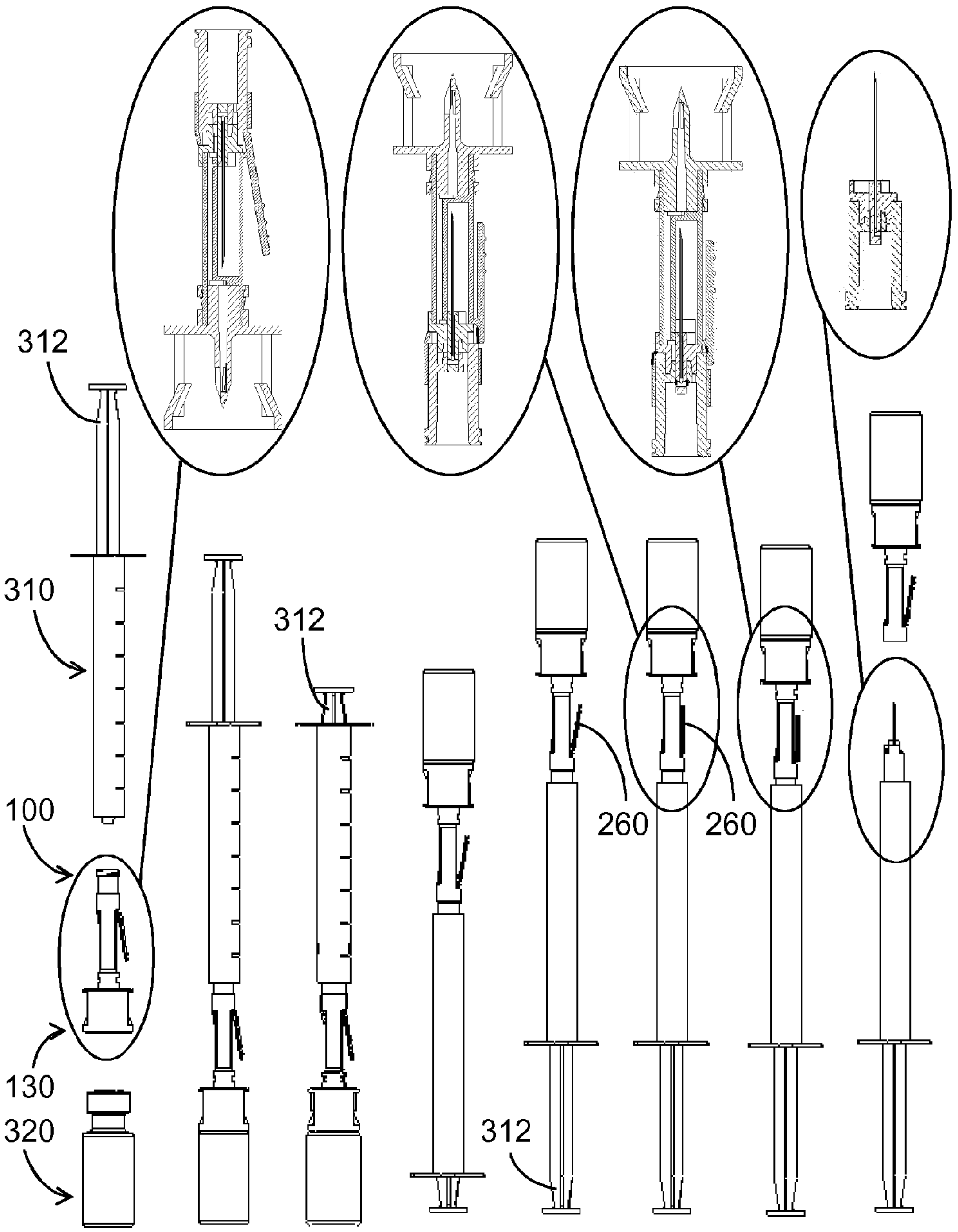
FIGS. 11A, 11B, 11C, 11D, 11E, 11F, 11G & 11H are simplified side view illustrations indicating various stages in the operation of the apparatus of FIGS. 1-10B.

FIGS. 11A, 11B, 11C, 11D, 11E, 11F, 11G & 11H are simplified side view illustrations indicating various stages in the operation of the apparatus of FIGS. 1-10B. FIG. 11A illustrates attaching of needleless syringe 310 to syringe attachment element 100 and insertion of vial 320 into second portion 130. FIG. 11B shows needleless syringe 310 fully attached to syringe attachment element 100 and vial 320 fully inserted into second portion 130, it being appreciated that removal of vial 320 from second portion 130 following full insertion thereof is very difficult or impossible.

FIG. 11C shows liquid from syringe 310 being drawn into vial 320. This is achieved by a user, holding the apparatus of FIG. 1 with attached syringe 310 and vial 320 in a generally vertical orientation as shown, pushing the plunger 312.

FIG. 11D illustrates mixed medicament in vial 320 and the apparatus of FIG. 1 with attached syringe 310 and vial 320 turned to opposite position as shown.

FIG. 11E shows liquid from vial 320 being drawn into syringe 310. This is achieved by a user, holding the apparatus of FIG. 1 with attached syringe 310 and vial 320 in a generally vertical orientation as shown, pulling the plunger 312.

FIG. 11F illustrates pressing inwardly on hand engageable lever 260.

FIG. 11G shows relative axial displacement of injection needle assembly 102 and syringe attachment element 100 by pushing of the medicament mixing chamber engagement assembly 120, containing vial 320.

FIG. 11H illustrates removal of the medicament mixing chamber engagement assembly 120, containing vial 320, from the apparatus of FIG. 1

FIGS. 12A, 12B, 12C and 12D are sectional illustrations of syringe attachment element 100, of needle base 108 and medicament mixing chamber engagement assembly 120 in FIGS. 11A-11H.

Figure 12A:
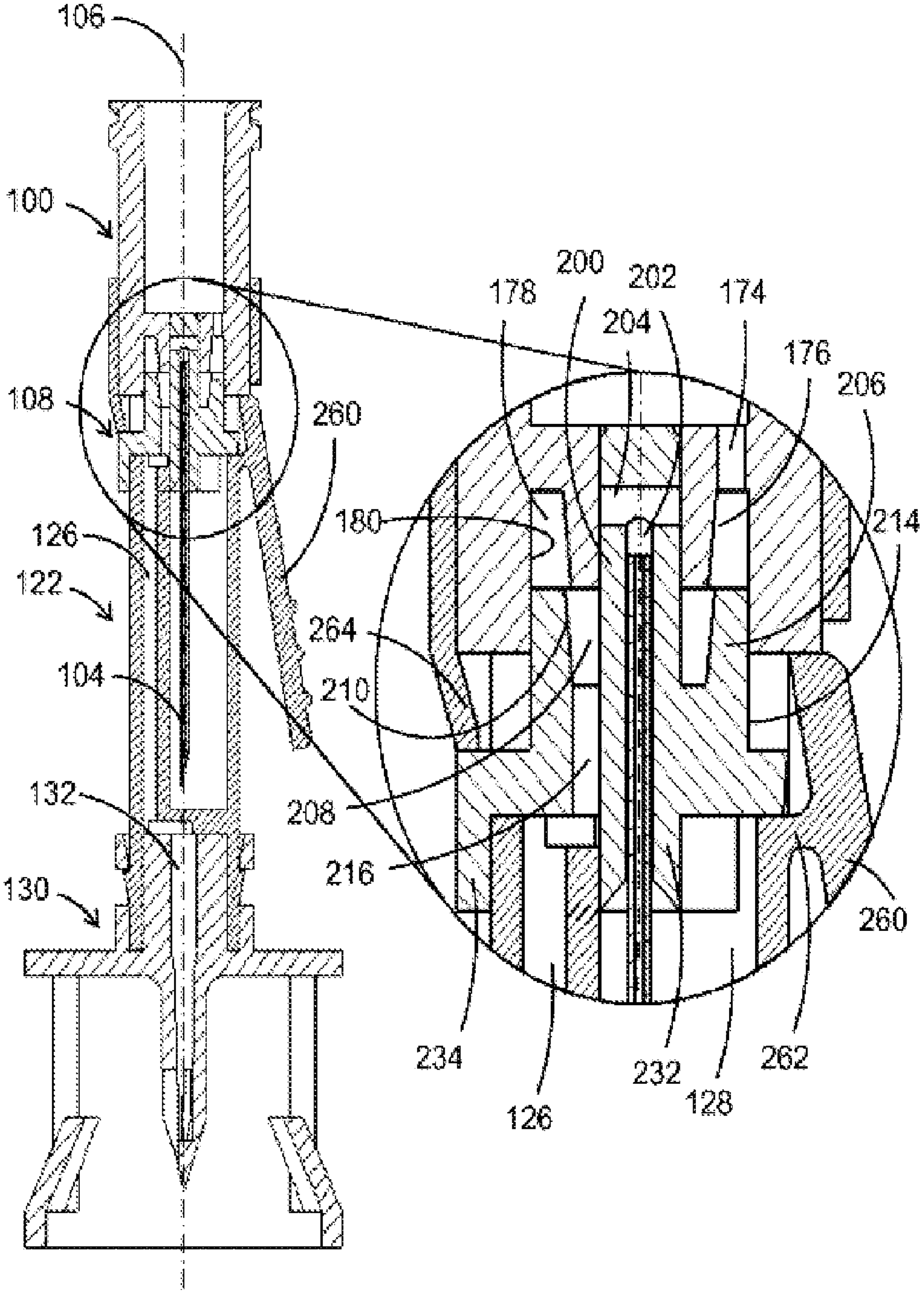
FIG. 12A is a sectional illustration of the relative orientations of the syringe attachment element, the needle base and medicament mixing chamber engagement assembly in FIGS. 11A-11E.

FIG. 12A is a sectional illustration of the first relative engagement orientation of the syringe attachment element 100, the needle base 108 and medicament mixing chamber engagement assembly 120 in FIGS. 11A-11E are configured to permit liquid communication between an interior of the needleless syringe (not shown) and the medicament mixing chamber (not shown) via passageway 152, side bore 174 and recess 178 of the syringe attachment element 100, recess 208 and liquid conduit 216 of the needle base 108, first liquid conduit portion 126 of first portion 122 and hollow spike 296 with apertures 298 of second portion 130. It is seen hand engageable lever 260 prevents providing relative axial displacement from first relative engagement orientation to second relative engagement orientation and inwardly facing retaining protrusion 264 is against shoulder surface 224 prevents the removal of medicament mixing chamber engagement assembly 120 from needle base 108.

Figure 12B:
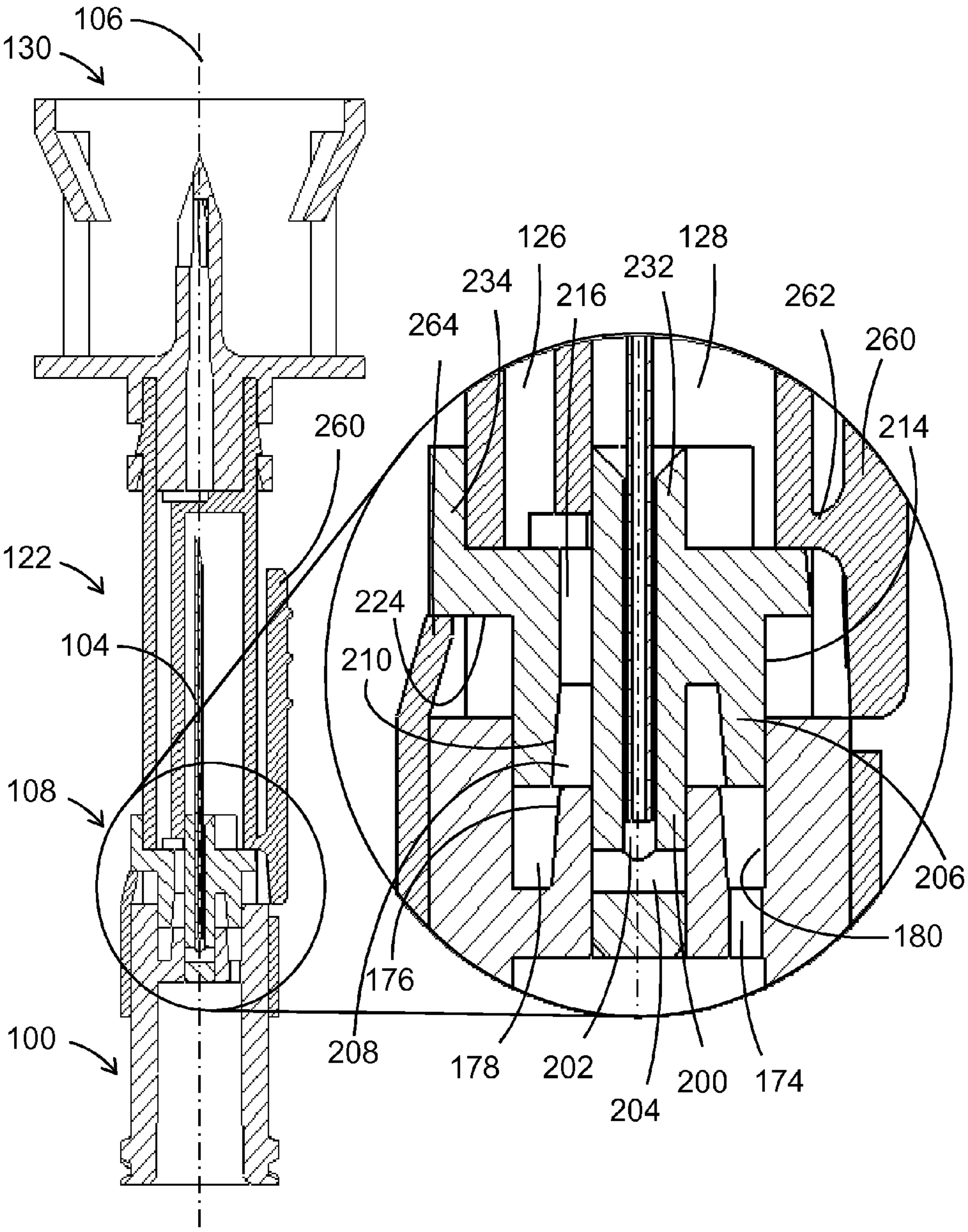
FIG. 12B is a sectional illustration of the relative orientations of the syringe attachment element, of the needle base and medicament mixing chamber engagement assembly in FIG. 11F.

FIG. 12B is a sectional illustration of the first relative engagement orientation of the syringe attachment element 100, the needle base 108 and medicament mixing chamber engagement assembly 120 in FIG. 11F. It is seen that hand engageable lever 260 permits providing relative axial displacement from first relative engagement orientation to second relative engagement orientation by pressing inwardly on hand engageable lever 260.

Figure 12C:
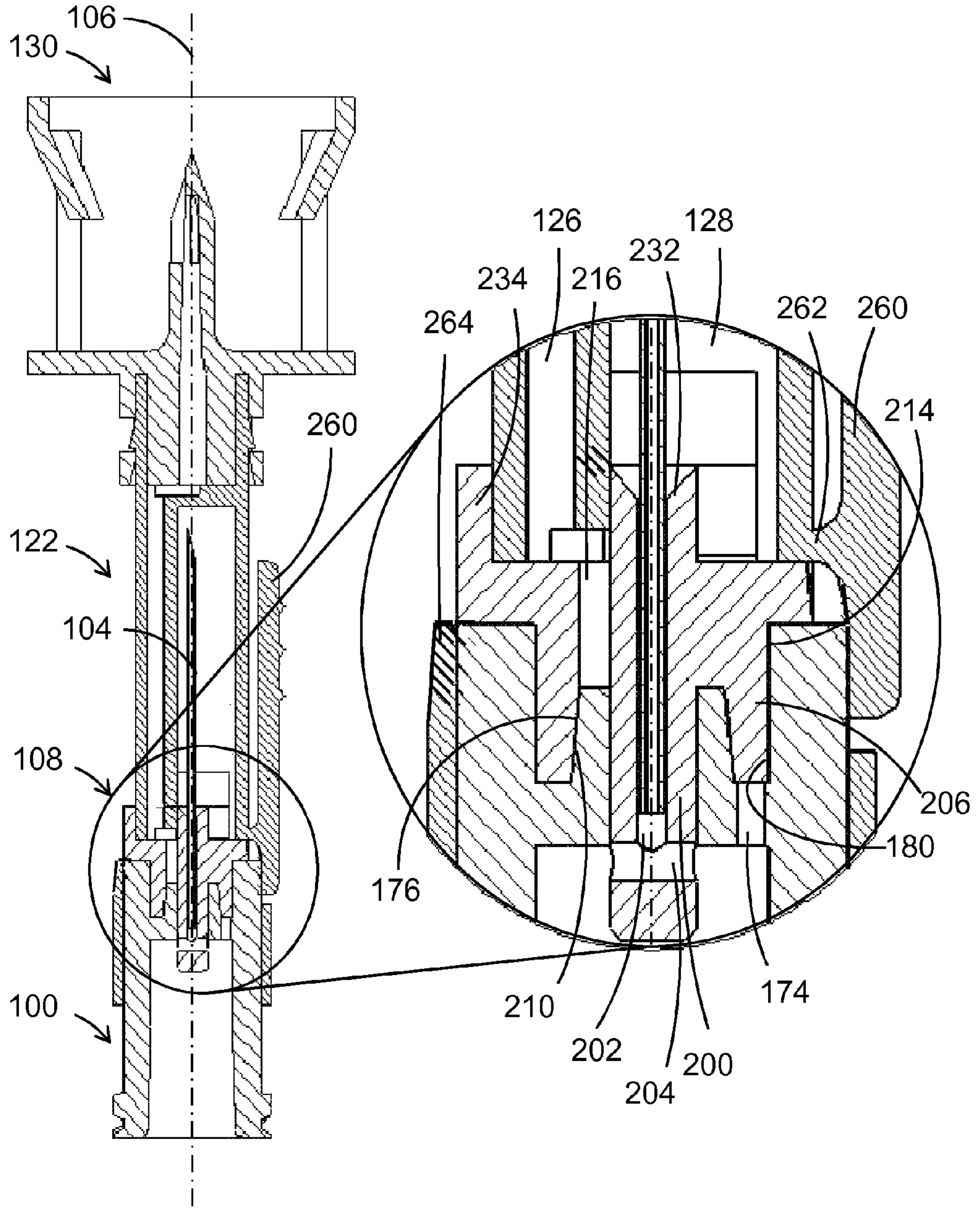
FIG. 12C is a sectional illustration of the relative orientations of the syringe attachment element, of the needle base and medicament mixing chamber engagement assembly in FIG. 11G.

FIG. 12C is a sectional illustration of the second relative engagement orientation of the syringe attachment element 100, the needle base 108 and medicament mixing chamber engagement assembly 120 in FIG. 11G are configured to permit liquid communication between an interior of the needleless syringe (not shown) and needle 104 via passageway 152 of the syringe attachment element 100, liquid communications bore 204 and axial needle retaining bore 202 of the needle base 108. It is seen that intermediate cylindrical portion 206 inserted into recess 178 for prevention liquid communication between an interior of the needleless syringe (not shown) and the medicament mixing chamber (not shown) and protrusion 264 permits removal of medicament mixing chamber engagement assembly 120 from needle base 108 by pressing outwardly on protrusion 264 from shoulder surface 224.

Figure 12D:
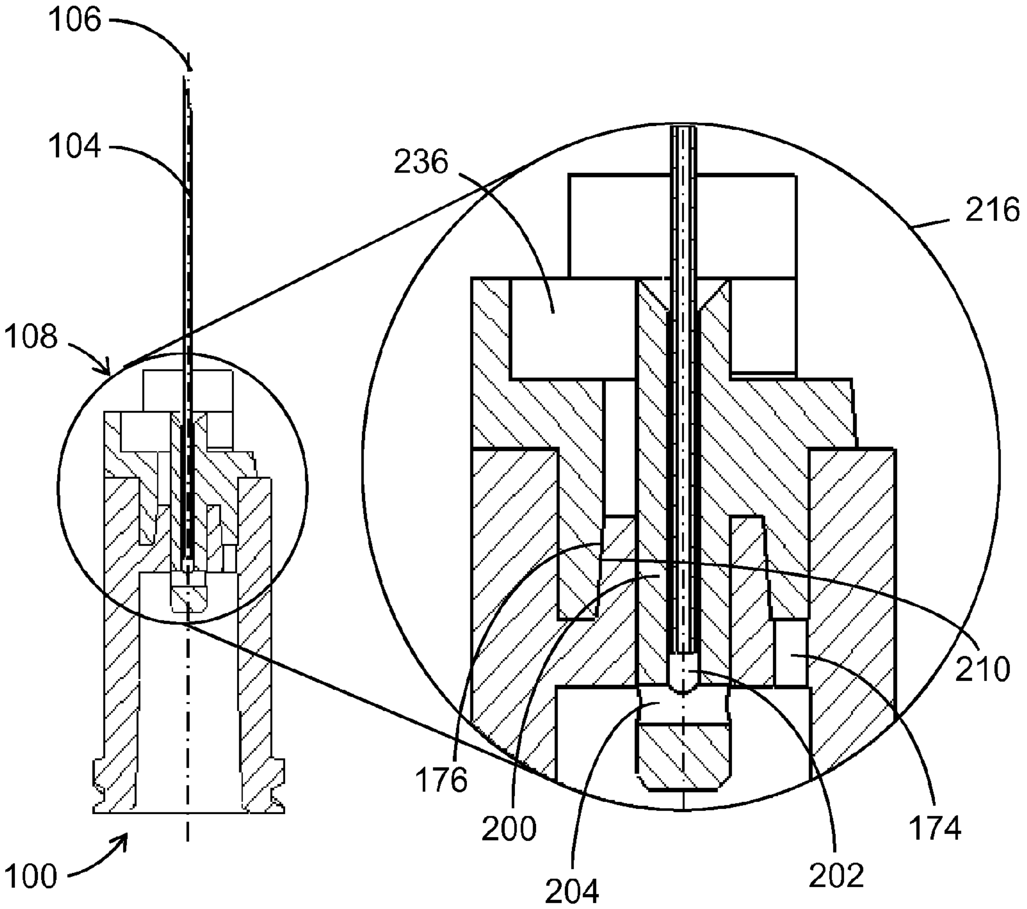
FIG. 12D is a sectional illustration of the relative orientations of the syringe attachment element and of the needle in FIG. 11H.

FIG. 12D is a sectional illustration of the relative orientations of the syringe attachment element 100 and the needle base 108 in FIG. 11H when apparatus of FIG. 1 ready to inject stage.

The invention claimed is:

1. Medicament mixing and injection apparatus comprising:

an injection needle assembly including a needle extending along an injection axis and a needle base to which said needle is fixed;

a syringe attachment element configured at a first axial end thereof to receive a needleless syringe and a second axial end thereof to engage said needle base in at least first and second relative engagement orientations which are mutually axially separated along said injection axis; and a medicament mixing chamber engagement assembly including:

an intermediate portion having a hand-engageable portion, said intermediate portion including a needle chamber surrounding said needle and a first liquid conduit portion, sealed from said needle chamber; and a medicament mixing chamber engagement portion including a second liquid conduit portion communicating with said first liquid conduit portion and configured for communication with a medicament mixing chamber, said syringe attachment element and said needle base being configured to:

(i) when said syringe attachment element and said needle base are in said first relative engagement orientation, permit liquid communication between an interior of said needleless syringe and said first liquid conduit portion and prevent liquid communication between the interior of the needleless syringe and the needle, and (ii) when said syringe attachment element and said needle base are relatively axially displaced along said injection axis such that said syringe attachment element and said needle base are in said second relative engagement orientation, permit liquid communication between an interior of said needleless syringe and said needle and prevent liquid communication between the interior of the needleless syringe and the first liquid conduit portion, the second relative engagement orientation being axially separated from said first relative orientation along said injection axis.

2. Medicament mixing and injection apparatus according to claim 1 and wherein operation of said hand engageable portion enables relative axial movement of said needle base and said syringe attachment portion from said first relative orientation along said injection axis to said second relative orientation along said injection axis.

3. Medicament mixing and injection apparatus according to claim 1 and wherein said intermediate portion and said medicament mixing chamber engagement portion are formed as separate elements.

4. Medicament mixing and injection apparatus according to claim 1 and wherein said medicament mixing chamber engagement assembly is integrally formed as one piece.

5. A medicament mixing and injection method comprising:

providing a medicament mixing and injection assembly including a needle extending along an injection axis and a needle base to which said needle is fixed, a syringe attachment element configured at a first axial end thereof to receive a needleless syringe and a second axial end thereof to engage said needle base in at least first and second relative engagement orientations which are mutually axially separated along said injection axis and a medicament mixing chamber engagement assembly;

associating a medicament mixing chamber with said medicament mixing chamber engagement assembly;

attaching a syringe to said syringe attachment element;

mixing a medicament in said medicament mixing chamber when said syringe attachment element and said needle base are in said first relative engagement orientation to permit liquid communication between the medicament mixing chamber and the syringe and to prevent liquid communication between the syringe and the needle, and drawing mixed medicament into said syringe;

providing relative axial displacement of said needle base and said syringe attachment element along said injection axis—such that said syringe attachment element and said needle base are in said second relative engagement orientation to permit liquid communication between the syringe and the needle and to prevent liquid communication between the syringe and the medicament mixing chamber;

disengaging said medicament mixing chamber engagement assembly from said syringe attachment element; and injecting the mixed medicament from said syringe through said needle.

6. A medicament mixing and injection method according to claim 5 and wherein said medicament mixing chamber engagement assembly includes a needle chamber surrounding said needle and a liquid conduit portion, sealed from said needle chamber and said syringe attachment element and said needle base are configured to permit liquid communication between an interior of said needleless syringe and said first liquid conduit portion when said syringe attachment element and said needle base are in said first relative engagement orientation and to permit liquid communication between an interior of said needleless syringe and said needle when said syringe attachment element and said needle base are in said second relative engagement orientation, axially separated from said first relative orientation along said injection axis.

7. A medicament mixing and injection method according to claim 5 and wherein said medicament mixing chamber engagement assembly includes a hand engageable portion which selectably enables relative axial movement of said needle base and said syringe attachment portion from said first relative orientation along said injection axis to said second relative orientation along said injection axis.

* * * * *